(12) United States Patent
McQuade et al.

(10) Patent No.: US 8,426,630 B2
(45) Date of Patent: Apr. 23, 2013

(54) METHOD AND APPARATUS FOR CONTINUOUS FLOW SYNTHESIS OF IBUPROFEN

(75) Inventors: D. Tyler McQuade, Tallahassee, FL (US); Andrew Bogdan, State College, PA (US); Sarah Lihoa Poe, Chestnut Hill, MA (US)

(73) Assignee: Florida State University Research Foundation, Tallahassee, FL (US)

( * ) Notice: Subject to any disclaimer, the term of this patent is extended or adjusted under 35 U.S.C. 154(b) by 159 days.

(21) Appl. No.: 12/868,787

(22) Filed: Aug. 26, 2010

(65) Prior Publication Data
US 2011/0054208 A1 Mar. 3, 2011

Related U.S. Application Data

(60) Provisional application No. 61/238,352, filed on Aug. 31, 2009.

(51) Int. Cl.
*C07C 69/612* (2006.01)
(52) U.S. Cl.
USPC .............................................. 560/1; 548/400
(58) Field of Classification Search .................. 548/400; 560/1
See application file for complete search history.

(56) References Cited

PUBLICATIONS

Tamura, Y. et al., Chem. Pharm. Bull. 33(3):1097-1103 (1985).*
Sheldon, R. A., J. Chem. Tech. Biotechnol., 68:381 (1997).
Anastas, P.T. et al., Acc. Chem. Res., 35:686 (2002).
Mason, B. P. et al., Chem. Rev., 107:2300 (2007).
Hessel, V., Curr. Org. Chem., 9:765 (2005).
Hessel, V., Chem. Eng. Technol., 28:267 (2005).
Hodge, P., Curr. Opin. Chem. Biol., 7:362 (2003).
Jas, G. et al., Chem. Eur. J., 9:5708 (2003).
Kirschning, A. et al., Angew. Chem., Int. Ed., 40:650 (2001).
Pennemann, H. et al., Org. Process Res. Dev., 8:422 (2004).
Watts, P. et al., Org. Biomol. Chem., 5:727 (2007).
Fukuyama, T. et al., Synlett, 2:151 (2008).
Ahmed-Omer, B. et al., Org. Biomol. Chem., 5:733 (2007).
Yoshida, J. et al., Chem. Eur. J., 14:7450 (2008).
Nagaki, A. et al., Org. Lett., 10:3937 (2008).
Nagaki, A. et al., Angew. Chem. Int. Ed., 47:7833 (2008).
Van Der Linden, J. M. J. et al., Org. Process Res. Dev., 12:911 (2008).
Bogdan, A. R. et al., Adv. Synth Catal, 351:849 (2009).
Hornung, C. H. et al., Org. Process Res. Dev., 11:399 (2007).
Acke, D. R. J. et al., Org. Process Res. Dev., 10:417 (2006).
Sahoo, H. R. et al., Angew. Chem. Int. Ed., 46:5704 (2007).
Baxendale, I. R. et al., Chem. Commun., 2566 (2006).
Baxendale, I. R. et al., Angew. Chem. Int. Ed., 48:4017 (2009).
Grant, D. et al., J. Org. Chem., 73:7219 (2008).
Bogdan, A. R. et al., Angew. Chem. Int. Ed., 46:1698-1701 [1728-1731] (2007).
Bogdan, A. R. et al., Beilstein Journal of Organic Chemistry, 5:17 (2009).
Poe, S. L. et al., J. Am. Chem. Soc., 128:15586 (2006).
Poe, S. L. et al., J. Am. Chem. Soc., 129:9216 (2007).
Roberts, R. M. G. et al., Tetrahedron, 39:137 (1983).
Effenberger, F. et al., Angew. Chem. Int. Ed., 11:300 (1972).
Singh, O.V. et al., Ind. J. Org. Chem., 28B:814 (1989).
Prakash, O. et al., Ind. J. Org. Chem., 289B:304 (1990).

* cited by examiner

*Primary Examiner* — Yong Chu
*Assistant Examiner* — Sonya Wright
(74) *Attorney, Agent, or Firm* — Alchemy-Partners, PC; Ajay A. Jagtiani (57) ABSTRACT

A multi-step method for the continuous synthesis of ibuprofen or a synthetic precursor of ibuprofen is provided that does not require any intermediate purification or isolation steps and uses reagents compatible with downstream reactions. According to some embodiments, a method is provided wherein isobutylbenzene and a propionyl compound may be converted into a first product in a first Friedel Crafts acylation reaction. The first product may then be converted into a second product in a 1,2-aryl migration reaction. Finally, the second product may be converted into ibuprofen in a hydrolysis reaction. The present invention also provides a method wherein only the first and second reaction steps or only the second and third reaction steps are performed. An apparatus is also provided having two or more microreactors and two or more junctions in particular arrangements for the synthesis of ibuprofen or a synthetic precursor of ibuprofen.

39 Claims, 3 Drawing Sheets

| Entry | Flow Rate [μL/min] | Residence Time [min] | T [°C] | Conversion[b] |
|---|---|---|---|---|
| 1 | 87.5 | 5 | 50 | 15% |
| 2 | 87.5 | 5 | 100 | 52% |
| 3 | 87.5 | 5 | 150 | 91%(70%)[c] |

METHOD AND APPARATUS FOR CONTINUOUS FLOW SYNTHESIS OF IBUPROFEN

CROSS-REFERENCE TO RELATED APPLICATION

This application claims benefit of priority to U.S. Provisional Application No. 61/238,352 filed Aug. 31, 2009, which is hereby incorporated by reference in its entirety.

GOVERNMENT INTEREST STATEMENT

This invention was made with support from the National Science Foundation pursuant to Grant No. CHE-0809261. The United States Government has rights to this invention.

FIELD OF THE INVENTION

The present invention relates to methods and apparatuses for the synthesis of the drug compound ibuprofen.

BACKGROUND

Organic synthesis is a powerful enterprise that continues to develop more selective and efficient chemical methods and synthetic routes. To synthesize complex molecules, whether in academic laboratories or industrial manufacturing, reactions are often performed iteratively in batch reactors. While these stepwise methods are powerful, they are also highly wasteful. The pharmaceutical industry, for example, produces 25-100 kg of waste for every kilogram of product synthesized. See, e.g., Sheldon, R. A., J. Chem. Tech. Biotechnol., 68:381 (1997). Though chemists are constantly striving to create more efficient syntheses, recent reminders of a resource-limited world underscore the need for more sustainable methods and technologies to synthesize molecules of importance. See, e.g., Anastas, P. T. et al., Acc. Chem. Res., 35:686 (2002). What is needed in the art is improved methods for the synthesis of organic drug compounds that efficiently utilize fewer reagents and reaction steps.

SUMMARY

According to a first broad aspect of the present invention, a method comprising the following steps: (a) reacting isobutylbenzene with a propionyl compound in the presence of a strong acid to produce a first product; and (b) reacting the first product with trimethyl orthoformate (TMOF) and an iodine-containing molecule to form a second product, wherein steps (a) and (b) are performed sequentially without an intervening isolation or purification step, and wherein step (b) is performed after step (a). According to some embodiments of the first broad aspect, the method may further comprise the step of (c) cooling the temperature of the reaction mixture comprising the first product of the reaction in step (a) and the TMOF and the iodine-containing molecule to about 0° C. just prior to step (b). According to embodiments of the first broad aspect, the method may further comprise the step of (d) reacting the second product of the reaction in step (b) with a strong base or nucleophilic catalyst to form ibuprofen, wherein steps (a), (b), and (d) are performed sequentially without an intervening isolation or purification step, and wherein step (d) is performed after steps (a) and (b).

The method of the first broad aspect may also be performed by a microreactor apparatus as described herein. According to embodiments of the first broad aspect, the reaction in step (a) may be performed in a first reagent stream in a first microreactor and the reaction in step (b) may be performed in a second reagent stream in a second microreactor, and wherein the first microreactor is positioned upstream of the second microreactor. The reaction in step (d) may also be performed in a third reagent stream in a third microreactor, wherein the second microreactor is positioned downstream of the first microreactor and upstream of the third microreactor.

According to a second broad aspect of the present invention, a method is provided comprising the following steps: (a) reacting 4-isobutylpropiophenone with a trimethyl orthoformate (TMOF) and an iodine-containing molecule to form a product; and (b) reacting the product with a strong base or nucleophilic catalyst to form ibuprofen, wherein steps (a) and (b) are performed sequentially without an intervening isolation or purification step, and wherein step (b) is performed after step (a).

According to a third broad aspect of the present invention, an apparatus is provided comprising a first microreactor and a second microreactor and a first junction and a second junction, wherein the first junction comprises a first inlet and a second inlet, wherein the outlet of the first junction is attached to or continuous with the inlet of the first microreactor, wherein the second junction comprises a third inlet attached to or continuous with the outlet of the first microreactor and a fourth inlet, wherein the outlet of the second junction is attached to or continuous with the inlet of the second microreactor, and wherein the second microreactor is positioned downstream of the first microreactor. According to some embodiments, the apparatus further comprises a third microreactor and a third junction, wherein the third microreactor comprises a fifth inlet and a sixth inlet, wherein the fifth inlet is attached to or continuous with the outlet of the second microreactor, and wherein the third microreactor is positioned downstream of the second microreactor. According to embodiments of the third broad aspect, the temperature of the first microreactor may be about 50° C. or higher, the temperature of the second microreactor may be about 50° C. or higher, the temperature of the second junction may be about 0° C., and/or the temperature of the third microreactor may be about 65° C. or higher.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION

Definitions

Where the definition of terms departs from the commonly used meaning of the term, applicant intends to utilize the definitions provided below, unless specifically indicated.

For purposes of the present invention, the term "microreactor" refers to an elongated tube for carrying a reagent stream that has a cross-sectional dimension that is sufficiently small to allow for highly efficient heat transfer with its surroundings and that has a sufficient length to achieve a desired residence time for the reagent stream. A microreactor may have an inlet on its upstream side and an outlet on its downstream side, which may each be attached to or continuous with an inlet or outlet of a junction. Tubes of a microreactor may be made of a resilient material to withstand the caustic nature of chemicals or solutions in a reagent stream. For example, a tube of a microreactor may comprise a resistant polymeric material, such as a polymer made of a resistant thermoplastic resin, such as a DuPont® fluoropolymer including Teflon® PFA, etc., or alternatively, a tube of a microreactor may comprise a metal material.

For purposes of the present invention, the term "junction" refers to an intersection of two or more channels that converge into one channel in the downstream direction of a microreactor apparatus, such as to combine two or more reagent streams. The two or more channels of a junction may each have an inlet on the upstream side of the junction that may either be (1) attached to or continuous with the outlet of a microreactor or (2) open to the exterior environment of a microreactor apparatus. If the inlet of one of the channels of the junction is open to the exterior environment of a microreactor apparatus, then it may provide a means to inject or input a reagent stream into the channel through its inlet, which may then mix or intermingle with another reagent stream in another channel of the junction. A junction may also have an outlet on the downstream side of the junction that may either be (1) attached to or continuous with the inlet of a microreactor or (2) open to the exterior environment of a microreactor apparatus. If the outlet of one of the channels of the junction is open to the exterior environment of a microreactor apparatus, then it may provide an output or outlet of a microreactor apparatus for the delivery or collection of a desired product of a reaction, such as ibuprofen or an intermediate or precursor thereof.

For purposes of the present invention, the term "microreactor apparatus" refers to an apparatus containing one or more microreactors, which may be joined by one or more junctions.

For purposes of the present invention, the term "channel" refers to the interior or lumen of a tube of a microreactor or a junction through which a reagent stream flows.

For purposes of the present invention, the term "reagent stream" refers to a mixture of reagents, solutions, and reaction components including reactants and products that is flowing through a channel at a given position of a microreactor and/or a junction.

For purposes of the present invention, the term "continuous" refers to one or more reagent stream(s) that flow continuously from one reaction step to the next without an intervening isolation or purification step.

For purposes of the present invention, the phrase "attached to or continuous with" refers to a connection between a microreactor and a junction that allows the reagent stream to continuously flow from the microreactor to the junction, or vice versa. The phrase "attached to or continuous with" may refer to a connection between a microreactor and a junction even if the microreactor and the junction are distinct objects but joined or fitted together.

For purposes of the present invention, the terms "precursor" or "synthetic precursor" may refer to a product or compound made during a sequence of reactions for the ultimate synthesis of ibuprofen. For example, a precursor may be a product of a Friedel-Crafts acylation reaction or a 1,2-aryl migration reaction according to embodiments of the present invention, such as 4-isobutylpropiophenone (compound 2) or methyl-2-(4-isobutylphenyl)propanoate (compound 3).

For purposes of the present invention, the term "propionyl compound" refers to a compound that may be used to provide a propionyl group for a Friedel-Crafts acylation according to embodiments of the present invention. For example, the term "propionyl compound" may refer to propionic acid, propionyl anhydride, or propionyl chloride, For purposes of the present invention, the term "residence time" refers to the time it takes for a molecule in a reagent stream to travel the entire length of a microreactor. The residence time for a reagent stream in a microrector may depend on the length and width of the microreactor as well as the flow rate of the reagent stream.

For purposes of the present invention, the term "upstream" refers to a direction that is counter to (i.e., in the opposite direction of) the general direction of flow of the reagent streams in a microreactor apparatus. For purposes of the present invention, the term "upstream side" refers to the side of an object, such as a microreactor or a junction, that is positioned in a microreactor apparatus facing in the upstream direction.

For purposes of the present invention, the term "downstream" refers to a direction that is in the same direction as the general direction of flow of the reagent streams in a microreactor apparatus. For purposes of the present invention, the term "downstream side" refers to the side of an object, such as a microreactor or a junction, that is positioned in a microreactor apparatus facing in the downstream direction.

Description

The present invention provides methods and/or apparatuses for the improved synthesis of ibuprofen, which may be achieved by a continuous process or set of reactions that do not require intermediate purification or isolation steps. It is theorized that new technologies, such as microreactors, may be applied to the organic synthesis of ibuprofen to improve its efficiency and resource utilization. Microreactors are a developing technology used to perform safer, more efficient and more selective chemical transformations in microchannels or narrow-bore tubing. See, e.g., Mason, B. P. et al., *Chem. Rev.*, 107:2300 (2007); Hessel, V., *Curr. Org. Chem.*, 9:765 (2005); Hessel, V., *Chem. Eng. Technol.*, 28:267 (2005); Hodge, P., *Curr. Opin. Chem. Biol.*, 7:362 (2003); Jas, G. et al., *Chem. Eur. J.* 9:5708 (2003); Kirschning, A. et al., Angew. *Chem., Int. Ed.*, 40:650 (2001); Pennemann, H. et al., *Org. Process Res. Dev.*, 8:422 (2004); Wirth, T., Ed. "Microreactors in Organic Synthesis and Catalysis," Wiley-VCH (Weinheim, 2008); Watts, P. et al., *Org. Biomol. Chem.*, 5:727 (2007); Fukuyama, T. et al., *Synlett*, 2:151 (2008); and Ahmed-Omer, B. et al., *Org. Biomol. Chem.*, 5:733 (2007), the entire contents and disclosures of which are hereby incorporated by reference.

The many advantages associated with running reactions in flow are attributed to large surface area-to-volume ratios. The small dimensions of microreactors allow for precise reaction control through rapid heat transfer and mixing that cannot be obtained in batch reactors. See, e.g., Yoshida, J. et al., *Chem. Eur. J.*, 14:7450 (2008); Nagaki, A. et al., *Org. Lett.*, 10:3937

(2008); Nagaki, A. et al., *Angew. Chem. Int. Ed.*, 47:7833 (2008); and van der Linden, J. M. J. et al., *Org. Process Res. Dev.*, 12:911 (2008), the entire contents and disclosures of which are hereby incorporated by reference. Scale-up of syntheses is also readily achieved by running a single reactor for extended periods of time or by the addition of more identical flow reactors in parallel, a process known as "numbering up." See, e.g., Bogdan, A. R. et al., *Adv. Synth Catal*, 351:849 (2009); Ehrfeld, W. et al., "Microreactors: New Technology for Modern Chemistry," Wiley-VCH (Weinheim, 2000); Hornung, C. H. et al., *Org. Process Res. Dev.*, 11:399 (2007); and Acke, D. R. J. et al., *Org. Process Res. Dev.*, 10:417 (2006), the entire contents and disclosures of which are hereby incorporated by reference.

According to a broad aspect of the present invention, a three-step continuous flow reaction scheme for the synthesis of ibuprofen is developed and described herein that eliminates the need for purification and isolation steps, which may also utilize microreactor(s). Microreactors have benefits and advantages due to their high surface area to volume ratio that allows for the temperature, flow rate, residence time, molar ratios, mixing, etc. of a reaction to be precisely controlled. There may be some limitations on the widths or diameters for the channel of a microreactor that may be used effectively to achieve these benefits and advantages. Large microreactor diameters (e.g., 2-3 inches or greater) may not have efficient heat transfer to the complete cross section of the reaction flow, thus reducing or eliminating the advantages of the microreactor. According to embodiments of the present invention, the diameter or width of the channel of a microreactor may be sufficiently small to allow for rapid and precise control of temperature of the reagent stream. On the other hand, extremely small widths or diameters for a microreactor channel (e.g., 100 nanometers or less) may resist or impede flow or become easily plugged or blocked. According to embodiments of the present invention, the diameter or width of the channel of a microreactor may be sufficiently large to avoid blockage or impeded flow. According to some embodiments, the diameter of width of the channel of a microreactor may be in a range of from about 100 microns to about 1 centimeter.

While the majority of microreactor work in organic synthesis has focused on single-step reactions, recent examples have demonstrated that multi-step reaction sequences may be conducted in flow. See, e.g., Yoshida, J. (2008), supra; Sahoo, H. R. et al., *Angew. Chem. Int. Ed.*, 46:5704 (2007); Baxendale, I. R. et al., *Chem. Commun.*, 2566 (2006); Baxendale, I. R. et al., *Angew. Chem. Int. Ed.*, 48:4017 (2009); Grant, D. et al., *J. Org. Chem.*, 73:7219 (2008), the entire contents and disclosures of which are hereby incorporated by reference. There is interest in the development of new methodologies that enable the rapid and efficient synthesis of important small molecules. See, e.g., Bogdan, A. R. et al., *Angew. Chem. Int. Ed.*, 46:1698 (2007); Bogdan, A. R. et al., *Beilstein Journal of Organic Chemistry*, 5:17 (2009); Poe, S. L. et al., *J. Am. Chem. Soc.*, 128:15586 (2006); and Poe, S. L. et al., *J. Am. Chem. Soc.*, 129:9216 (2007), the entire contents and disclosures of which are hereby incorporated by reference.

Multi-step reaction sequences may be carried out in one pot (i.e., in batch) or in series (e.g., with microreactors). For batch reactions, independent reactions steps are performed in series with isolation and purification of compounds between individual reaction steps. In contrast, for continuous flow with multi-step synthesis of organic compounds, it is important (if not essential) that reaction components or reagent streams be chosen such that they do not affect downstream reaction steps since compounds are not isolated or purified between each of the reaction steps. Thus, a retrosynthetic analysis of ibuprofen is performed to consider the entire set of continuous synthesis reactions as a whole while paying careful attention to reaction compatibilities. For continuous synthesis, reactions must be designed such that byproducts and excess starting materials from one reaction are compatible with downstream reactions. By doing so, reactions may be performed in sequence without breaks in the synthesis process, which may minimize time, cost and human involvement in the synthesis process.

Figure 1:
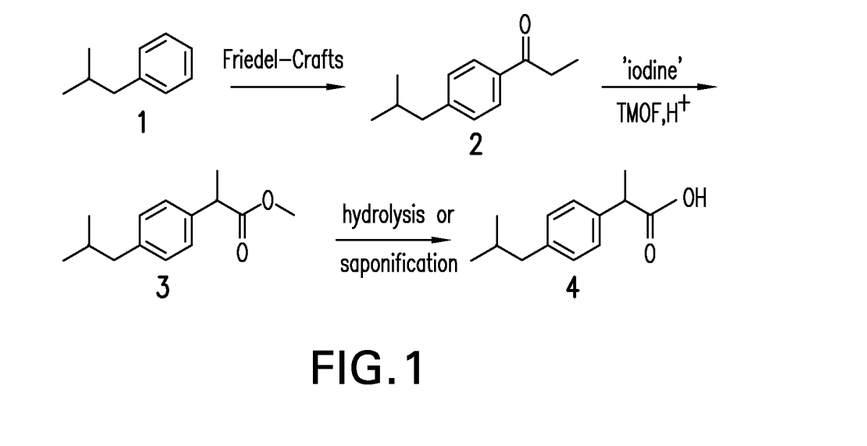
FIG. 1 is a drawing of a three-step scheme for the continuous synthesis of ibuprofen.

According to embodiments of the present invention, a general three-step reaction scheme for the continuous flow synthesis of ibuprofen is outlined in FIG. 1. However, some embodiments of the present invention may only comprise two of the three steps of this reaction scheme. See, e.g., Y. Tamura, T. et al., *Chem. Pharm. Bull.* 33(3):1097-1103 (1985). Although the general reaction scheme provided in FIG. 1 may be similar to that described in Y. Tamura, T. et al. (1985), supra, embodiments of the present invention make several key changes to prior methods that allow for the continuous synthesis of ibuprofen. In fact, the reaction scheme described in Tamura, T. et al. is a batch synthesis that would not be compatible with the continuous synthesis of ibuprofen according to embodiments of the present invention.

In a first or F-C reaction step of the present invention, isobutylbenzene (IBB; compound 1) is converted to 4-isobutylpropiophenone or 1-(4-isobutylphenyl)propan-1-one (compound 2) (see FIG. 1). The first reaction step may utilize a Friedel-Crafts (F-C) acylation reaction to convert IBB along with a propionyl compound, such as propionic acid, into compound 2. Conventionally, Friedel-Crafts acylation of IBB used in the synthesis of ibuprofen is carried out in the presence of a weak Lewis acid, such as aluminum chloride ($AlCl_3$), in a first reaction step, which may "activate" the propionyl compound into an acylating agent (i.e., to make the propionyl compound become sufficiently electrophilic to drive the F-C reaction and react with IBB). A Lewis acid may be defined as an electron deficient molecule that serves as an electron acceptor in a reaction and may be distinguished from a Brønstead acid in that a Lewis acid may not be a proton donor. Lewis acids have been chosen for Friedel-Crafts acylation because of their selective and controlled reactivity in their discrimination of where to acquire electrons in a reaction. In contrast, strong proton-donating Brønstead acids have generally been avoided for use in Friedel-Crafts acylation reactions because of their tendency to isomerize chemical groups and to produce a mixture of undesired byproducts. An exception to this may include a weak Brønstead acid, such as hydrofluoric acid (HF), which has been used in place of a Lewis acid in a F-C acylation reaction. However, HF is not preferred because of its extremely dangerous and corrosive properties. Despite the high product yield achieved using $AlCl_3$ as the acid in a Friedel-Crafts acylation reaction with IBB and propionic acid, $AlCl_3$ is not compatible with downstream reaction steps and therefore cannot be used in the present reaction scheme for the continuous synthesis of ibuprofen without intermediate isolation or purification steps.

According to embodiments of the present invention and in contrast to conventional methods, it is discovered through experimentation surveying multiple conditions that a very strong Brønstead acid (e.g., trifluoromethanesulfonic acid, triflic acid, or TfOH), may in fact be used in the synthesis of compound 2 from IBB and propionic acid in the first reaction step of the present scheme without significantly isomerizing chemical groups or producing a mixture of undesired products. See, e.g., Roberts, R. M. G. et al., *Tetrahedron*, 39:137 (1983); and Effenberger, F. et al., *Angew. Chem. Int. Ed.*, 11:300 (1972). Without being bound by any theory, it is proposed that the reaction of triflic acid with propionic acid may lead to the generation of a mixed anhydride, a very active acylating agent. The positive result with triflic acid is surprising given the belief that moderate and strong Brønstead acids generally cause problems with F-C reactions as noted above. Importantly and unlike $AlCl_3$, TfOH is found to be compatible with the downstream reaction steps of the present reaction scheme for the continuous synthesis of ibuprofen.

According to embodiments of the present invention and in contrast to conventional methods, a strong acid may be used in a first or F-C reaction step to "activate" the propionyl compound. According to embodiments of the present invention, the strong acid may include a strong Brønstead acid, which may have a pKa value of less than or equal to 1.0. The acid must be able to react with a propionyl compound, such as propionic acid, to form an "activated" species (a protonated or dehydrated form of the carboxylic acid) of the propionyl compound. According to some embodiments, the strong acid may be a sulfonate acid, such as triflic acid (TfOH) or toluene sulfonic acid, or other superacid, such as fluorosulfonic acid or fluoroantimonic acid or any acid with pKa lower than sulfuric acid. In addition, the propionyl compound in the first F-C acylation reaction step may include, for example, propionic acid, propionyl anhydride, propionyl chloride, or any other propionyl compound that may be used to provide the propionyl group in forming compound 2 during the first F-C reaction step.

Figure 2:
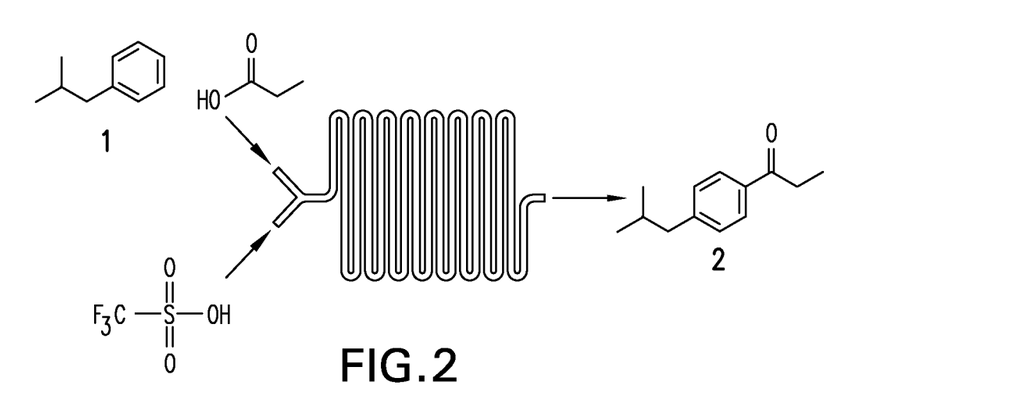
FIG. 2 is a drawing of a microreactor setup for a Friedel-Crafts acylation reaction.

According to embodiments of the present invention, the F-C reaction step may be carried out in a microreactor to achieve a desired molar ratio(s) of reagents, residence time, temperature, etc. for the reaction. As stated above, microreactors have advantages due to their high surface area to volume ratio that allow for the temperature, flow rate, residence time, molar ratios, mixing, etc. to be precisely controlled. According to some embodiments, the flow rates or molar ratios of the reagents in the F-C reaction step may be controlled. For example, a solution or reagent stream of IBB (compound 1) and a propionyl compound, such as propionic acid, in one reagent stream may be mixed with another reagent stream containing a strong acid, such as TfOH, at a first junction (See FIG. 2). This may be achieved by a Y- or T-junction to join the two streams before entering the combined channel of the microreactor. The isobutylbenzene and the propionyl compound may be inputted into one inlet of a first junction, and the strong acid may be inputted into another inlet of the first junction with the first junction attached to or continuous with the upstream side or inlet of a first microreactor. According to some embodiments, the ratio of equivalents of the acid (e.g., triflic acid) to IBB that are combined or mixed at the first junction may be about 3:1 or greater. Alternatively, according to some embodiments, the ratio of equivalents of the acid (e.g., triflic acid) to IBB that are combined or mixed at the first junction may be about 5:1 or greater. However, the ratio of equivalents of the acid (e.g., triflic acid) to IBB should be no greater than 100:1. It is also conceivable that the ratio of equivalents of the acid to IBB may be as low as 0.001:1 although generally less preferred. The ratio of equivalents of the acid to IBB may depend on many factors including the particular reaction conditions, identity of the acid, reaction time, etc. For example, the various flow rates of reaction components or reagent streams may be varied or controlled by application of a manual or automated syringe, pump, etc. If the F-C reaction is performed in a flow microreactor, it may be critical that unions and junctions as well as tubes, etc. of a microreactor each comprise a resistant polymeric material, such as a polymer made of a resistant thermoplastic resin, such as a DuPont® fluoropolymer including Teflon® PFA, etc., to withstand the caustic nature of TfOH. Alternatively, unions and junctions as well as tubes of a microreactor may each comprise a metal material.

According to some embodiments, the "residence time" of the reaction components or reagent stream in the microreactor of the first F-C acylation reaction step may be controlled. The residence time may be described as the time it takes for a molecule to travel the length of the microreactor, which may depend on a combination of different factors, such as the width and length of the channel as well as the flow rate of the reagent stream. For example, the residence or reaction time of reaction components or reagent stream in the microreactor of the first F-C acylation reaction step may be about 5 minutes or greater, but no greater than 4 days. However, it is conceivable that the residence or reaction time for the acylation reaction step may be as short as about 1 second depending on the reaction conditions although generally less preferred. The temperature may depend on many factors, such as the flow rate of the reagent stream through a microreactor.

Figure 3:
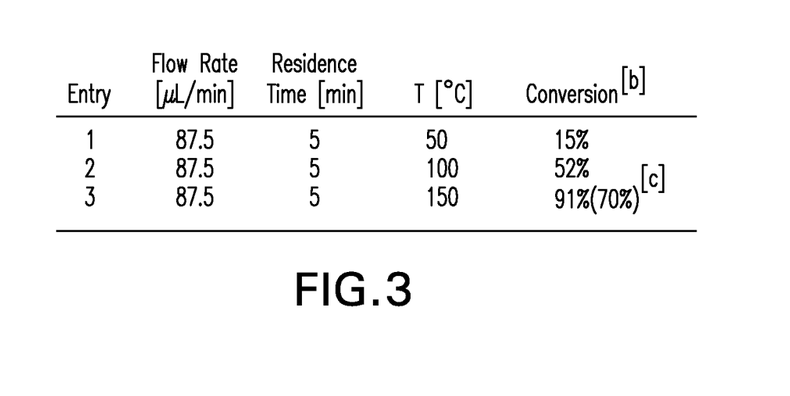
FIG. 3 is a table showing the optimization of the flow Friedel-Crafts acylation.

According to embodiments of the present invention, the temperature of the microreactor for the first F-C acylation reaction step may be controlled. In one example, when the reagent streams of (1) IBB plus propionic acid and (2) TfOH are combined at a T-junction (or tee junction), "plug flow" may result due to the possible immiscibility of these reagents at lower temperatures, such as 50° C. with a 5 minute residence time, and a low conversion rate may result. Plug flow is observed throughout the reactor to the reactor outlet under these conditions, suggesting that poor mixing and low temperatures may lead to low conversion. Although the reaction may become dark red as it proceeds, the plugs may appear colorless. Batch reactions with vigorous mixing at low temperature are also slow, thus indicating that mixing is not the only variable that impacts reaction rate. In this example, increasing the reaction temperature to 100° C. produced better results with increased conversion and decreased frequency in the formation of plugs, whereas 150° C. gave the highest conversion and yield (see table in FIG. 3). In one example, the reaction generated about 5% of the 1,2-adduct as indicated by GC and GC/MS, and this by-product is ultimately converted to the 1,2-derivative of ibuprofen in the continuous flow synthesis and removed after recrystallization. In this example, the plugs coalesce at 150° C. by visual inspection resulting in apparent homogeneity at the outlet stream of the reactor, thus indicating efficient mixing. Therefore, according to embodiments of the present invention, the temperature of the microreactor for the first F-C acylation reaction step may alternatively be about 50° C. or higher, about 100° C. or higher, or about 150° C. or higher. Standard reaction conditions were used for the reactions summarized in FIG. 3 including 1.0 equivalents of propionic acid and 5.0 equivalents of TfOH. Conversion was determined using gas chromatography (GC) with dodecane as an internal standard. The number in parenthesis in FIG. 3 corresponds to isolated yield after column chromatography.

According to embodiments of the present invention, the 4-isobutylpropiophenone (compound 2) synthesized in the first or F-C reaction of the present reaction scheme may then be converted into methyl-2-(4-isobutylphenyl)propanoate (compound 3) in a second reaction step. This reaction step of the present reaction scheme may be described as a "1,2-aryl migration" or a "Tamura rearrangement." It has been shown that the addition of acid to a mixture of aryl ketones, trimethyl orthoformate (TMOF), and $PhI(OAc)_2$ yields 2-arylpropanoates in high yield. See, e.g., Tamura, Y. et al. (1985), supra; Singh, O. V. et al., *Ind. J. Org. Chem.*, 28B:814 (1989); and Prakash, O. et al., Ind. *J. Org. Chem.*, 289B:304 (1990), the entire contents and disclosures of which are hereby incorporated by reference. However, other electrophiles or iodine containing molecules, such as $I_2$ or triflic anhydride, may be used in place of $PhI(OAc)_2$ in the reaction. This reaction is selected in part because it requires no transition metals and an iodobenzene byproduct of the reaction may be recycled. Iodobenzene is a byproduct of the 1,2-aryl migration, which may be converted back to $PhI(OAc)_2$ by treatment with peracetic acid.

Figure 4:
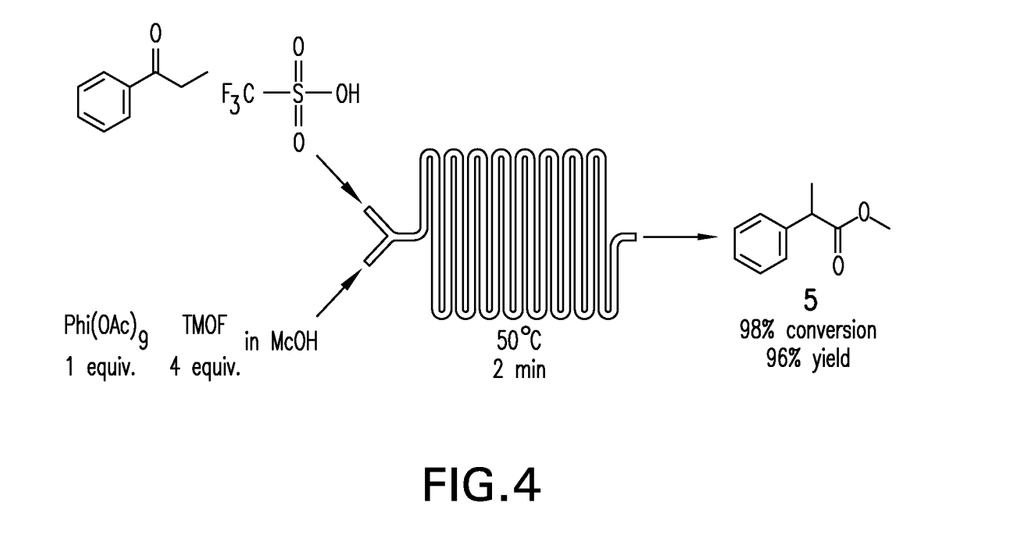
FIG. 4 is a drawing of a microreactor setup and reaction conditions for a flow PhI(OAc)$_2$-mediated 1,2-aryl migration reaction.

As stipulated above, in a continuous synthesis requiring no intermediate purification steps, all byproducts and excess reagents from prior steps must be compatible with downstream reactions. Therefore, it is essential that excess reagents (TfOH and unreacted IBB) used in the Friedel-Crafts acylation are compatible with the next step of our reaction sequence (i.e., the 1,2-aryl migration). In an experiment using propiophenone as a test substrate, the 1,2-aryl migration reaction is shown to be compatible with the strong TfOH from the first reaction step (see FIG. 4). In this test experiment, high yields of the methyl ester of the propiophenone test substrate (compound 5) are generated in a 1,2-aryl migration reaction despite the presence of TfOH with a 2 minute residence time at about 50° C. Not only do these test experiments demonstrate that TfOH from the first reaction step does not interfere with a 1,2-aryl migration reaction, products of the 1,2-aryl migration reaction may be generated with high yield. Thus, optimized conditions from these experiments may be used in the second reaction step of the present reaction scheme.

Figure 5:
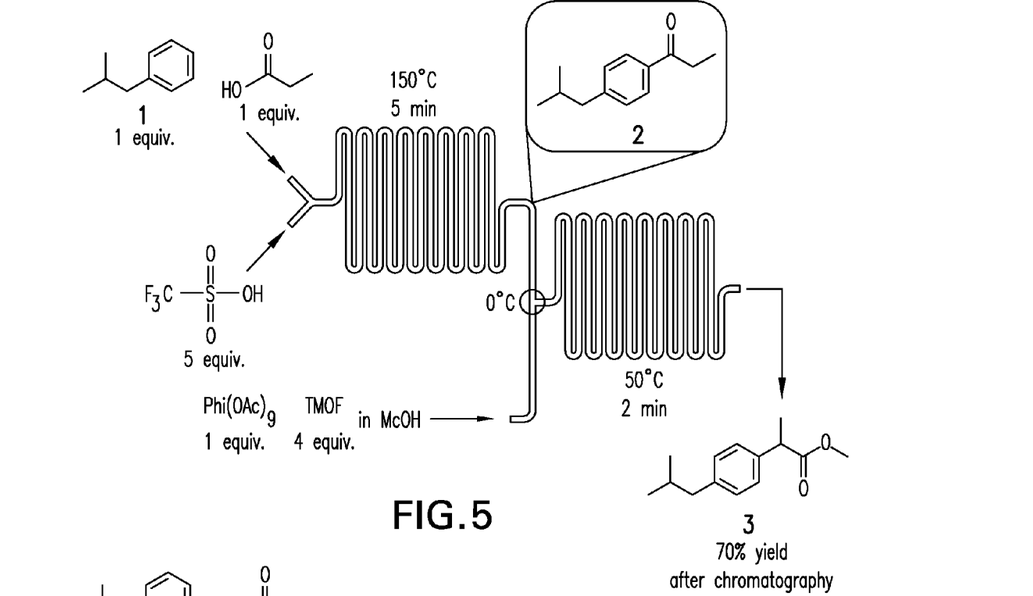
FIG. 5. is a drawing of a two-step reaction sequence and reaction conditions for the continuous synthesis of a precursor in the synthesis of ibuprofen.

With the first two reaction steps of the present reaction scheme tested separately, a system is assembled such that the product stream from the Friedel-Crafts acylation is immediately relayed into the 1,2-aryl migration using conditions derived from results obtained with the separately tested reaction steps (see FIG. 5). Not only does TfOH not interfere with the generation of products in the 1,2-aryl migration reaction in high yield, there is a further unanticipated benefit in that this two-step system requires no additional acid because the TfOH from the first Friedel-Crafts acylation reaction step actually facilitates (i.e., accelerates) the second 1,2-aryl migration reaction step.

According to embodiments of the present invention, the second or 1,2-aryl migration reaction step may be carried out in a microreactor to achieve a desired molar ratio(s) of reagents, residence time, temperature, etc. for the reaction. According to some embodiments, the flow rates or molar ratios of the reagents in the second or 1,2-aryl migration reaction step may be controlled. For example, the product of the F-C reaction step (4-isobutylpropiophenone; compound 2) from a first microreactor in one reagent stream may be mixed with another reagent stream of an electrophile, which may include an iodine-containing molecule, such as $I_2$, PhI(OAc)$_2$, triflic anhydride, etc., and TMOF in methanol (MeOH) (See FIG. 5) at a second junction. This may be achieved by a Y- or T-junction to join the two streams at the second junction before entering the combined channel of the second microreactor. The product of the F-C reaction may be inputted into one inlet of a second junction with the second junction attached to or continuous with the downstream side or outlet of a first microreactor, and the electrophile or iodine-containing molecule may be inputted into another inlet of the second junction. However, to achieve efficient mixing of the outlet stream from the first step with the PhI(OAc)$_2$/TMOF reagent stream for the second step, a modified tee (T-) junction may be used to improve mixing, such that the inner diameter is, for example, about 0.75 mm and packed with glass beads (e.g., about 250-300 µm).

In one experiment, it is found that cooling the junction used to combine the outlet stream from the first or F-C reaction step with the PhI(OAc)$_2$/TMOF reagent stream for the second or 1,2-aryl migration reaction step is necessary due to significant off-gassing that may otherwise occur, for example, at room temperature. In this example, it is found that cooling the tee junction to about 0° C. just upstream of the second microreactor and/or just prior to the second reaction step mixed the two streams effectively, resulting in about a 70% two-step yield after column chromatography, with quantitative conversion of the 4-isobutylpropiophenone into methyl-2-(4-isobutylphenyl)propanoate (compound 3). It is also important that this cooling step occur very quickly, if not nearly instantaneously. If the temperature prior to the second microreactor and/or second reaction step is not quickly cooled from a high temperature of the first reaction and/or microreactor, it is found that sufficient mixing may not occur, plugs may be formed, and undesired side products may be generated. Thus, according to embodiments of the present invention, the second junction may be cooled, such as to about 0° C., just upstream of the second microreactor and/or second reaction step. However, it is conceivable that the second junction may be cooled to a temperature as low as −50° C. or as high as 100° C., although temperatures much cooler than 100° C. may generally be preferred.

According to some embodiments, the ratio of equivalents of the TMOF to the iodine-containing molecule, such as $I_2$ or PhI(OAc)$_2$, in one stream may be about 4:1 or greater in the second or 1,2-aryl migration reaction step, but the ratio of equivalents of the TMOF to the iodine-containing molecule should be no greater than 100:1. However, it is conceivable that the ratio of equivalents of the TMOF to the iodine-containing molecule may be as low as 0.01:1 although generally less preferred. The ratio of equivalents of the TMOF to the iodine-containing molecule may depend on many factors including the particular reaction conditions, identity of the iodine-containing molecule, reaction time, etc. For example, the various flow rates of reaction components or reagent streams may be varied or controlled by application of a manual or automated syringe, pump, etc. and/or by the flow rate of an upstream reaction. According to some embodiments, the "residence time" of reaction components or reagent stream in the microreactor of the second or 1,2-aryl migration reaction step may be controlled. For example, the residence or reaction time in the microreactor of the 1,2-aryl migration reaction step may be about 2 minutes or greater, but no greater than 4 days. However, it is conceivable that the residence time may be as short as 1 second depending on the reaction conditions although generally less preferred. The residence time in the microreactor of the 1,2-aryl migration reaction step may depend on the particular conditions, such as the flow rate of the reagent stream through a microreactor. According to embodiments of the present invention, the temperature of the microreactor for the 1,2-aryl migration reaction step may be controlled. For example, the reaction temperature for the second or 1,2-aryl migration reaction step may be about 50° C. or higher, but no greater than 150° C. However, it is conceivable that the reaction temperature for the 1,2-aryl migration reaction step may be as low as −50° C. depending on the reaction conditions although generally less preferred. The reaction temperature for the 1,2-aryl migration reaction step may depend on many factors.

Figure 6:
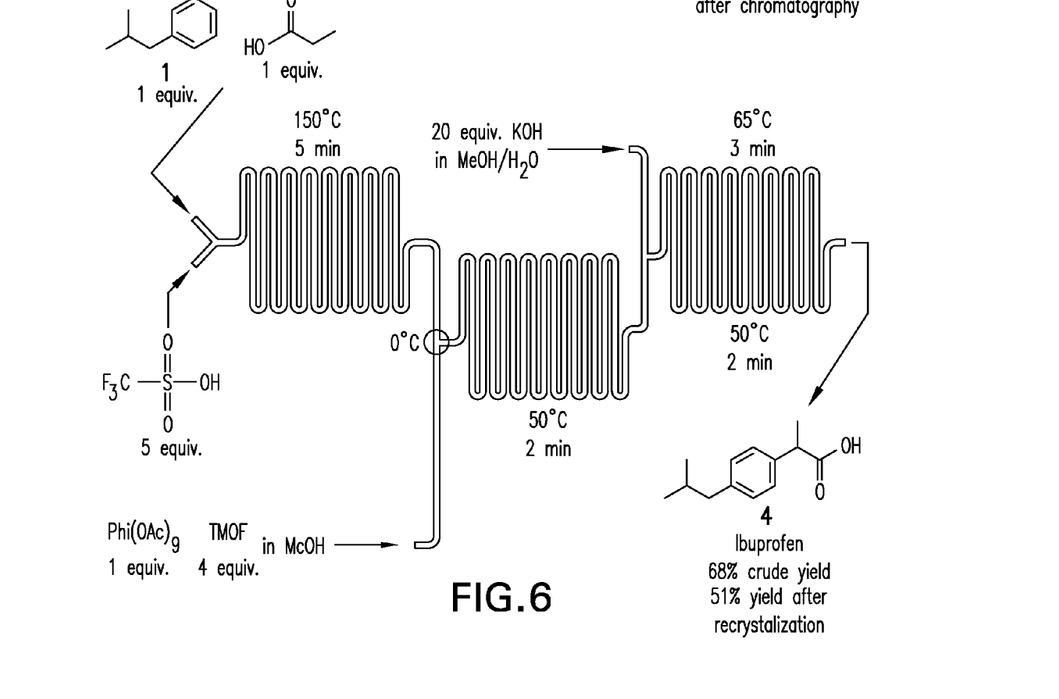
FIG. 6. is a drawing of the three-step reaction sequence and reaction conditions for the continuous flow synthesis of ibuprofen.

According to embodiments of the present invention, the methyl-2-(4-isobutylphenyl)propanoate (compound 3) synthesized in the second or 1,2-aryl migration reaction of the present reaction scheme may then be converted into ibuprofen (compound 4) in a subsequent reaction step (see FIGS. 1 and 6), which may be the third reaction in the three-step reaction scheme. This reaction step of the present reaction scheme may be described as a "hydrolysis," "saponification," or "saponifying" reaction by treatment of compound 3 from the second or 1,2-aryl migration reaction. Such a hydrolysis or saponification reaction may include an acid-catalyzed, base-catalyzed, or base-mediated hydrolysis reaction. For example, the hydrolysis reaction may use a strong base, such as a metal hydroxide including KOH, etc. However, other types of catalysts, such as nucleophilic catalysts, may be used in the hydrolysis reaction, such as pyridine, dimethyaminopyridine (DMAP), cyanide, etc.

According to embodiments of the present invention, the third or hydrolysis reaction step may be carried out in a microreactor to achieve a desired molar ratio(s) of reagents, residence time, temperature, etc. for the reaction. According to some embodiments, the flow rates or molar ratios of the reagents in the third or hydrolysis reaction step may be controlled. According to some embodiments, the product of the second or 1,2-aryl migration reaction step (compound 3) from the second microreactor in one reagent stream may be mixed with another reagent stream containing an excess amount (e.g., 1.1 to 1000 equivalents) of a base at a third junction relative to the number of moles of the product plus number of moles of the strong acid. This may be achieved by a Y- or T-junction to join the two streams at a third junction before entering the combined channel of the third microreactor. The product of the 1,2-aryl migration reaction may be inputted into one inlet of a third junction with the third junction attached to or continuous with the downstream side or outlet of a second microreactor, and the strong base or electrophilic catalyst may be inputted into another inlet of the third junction.

According to one example of the three-step reaction scheme, sampling of the outlet stream of the third microreactor showed the presence of only a residual IBB, iodobenzene, and trace amounts of compound 3. After an acidic work-up in this example, ibuprofen (compound 4) is obtained in 68% crude yield and 51% yield (99% purity by GC and NMR) after recrystallization. The low yield from the recrystallization in this example most likely stems from the recrystallization of ibuprofen on a small scale. When larger batches of ibuprofen are recrystallized, higher yields are obtained.

According to some embodiments, the amount of base added in the third or hydrolysis reaction step may be an amount effective to raise the pH to about 14. For example, the number of equivalents of the base added to the third reaction step relative to the number of equivalents of IBB and/or propionyl compound in the first reaction (and/or the iodine compound in the second reaction) may be about 20:1 or greater, but no greater than 1000:1. It is conceivable that the ratio of the number of equivalents of the base to the number of equivalents of IBB and/or propionyl compound from the first reaction may be as low as 0.01:1 although generally less preferred. The number of equivalents of the base added to the third reaction step relative to the number of equivalents of triflic acid in the first reaction may also be about 4:1 or greater, but no greater than 1000:1. It is also conceivable that the ratio of the number of equivalents of the base added to the third reaction step relative to the number of equivalents of triflic acid in the first reaction may be as low as 0.01:1 although generally less preferred. The number of equivalents of the base added to the third reaction step relative to the number of equivalents of TMOF in the second reaction may also be about 5:1 or greater but no greater than 1000:1. It is also conceivable that the ratio of the number of equivalents of the base added to the third reaction step relative to the number of equivalents of TMOF in the second reaction may be as low as 0.01:1 although generally less preferred. For example, the various flow rates of reaction streams may be varied or controlled by application of a manual or automated syringe, pump, etc. and/or by the flow rate of an upstream reaction.

One of the dangers with the third or hydrolysis reaction step is the addition of a strong base to a strongly acidic solution, which may increase the pH of the reaction flow from about 1.0 to about 14.0 over a short period of time. Under batch conditions, such a combination may produce a strongly exothermic or even explosive reaction. However, through the use of microreactors, the temperature may be controlled due to the excellent heat transfer, such that the exotherms are immediately taken out of the system and the reaction is controlled.

According to some embodiments, the "residence time" of reaction components or reagent stream in the microreactor of the hydrolysis reaction step may be controlled depending on many factors. For example, the residence time in the microreactor for the third hydrolysis reaction step may be about 3 minutes or greater, but no greater than 4 days. It is also conceivable that the residence or reaction time in the microreactor for the third hydrolysis reaction step may be as low as 0.01 seconds depending on the reaction conditions although generally less preferred. According to embodiments of the present invention, the temperature of the microreactor for the hydrolysis reaction step may be controlled depending on many factors. For example, the reaction temperature for the hydrolysis reaction step may be about 65° C. or higher, but not greater than 150° C.

A continuous flow synthesis of an active pharmaceutical ingredient, ibuprofen, is developed using an efficient three-step process that requires no intermediate purifications steps. Using less than 500 cm of tubing and five syringe pumps, the flow synthesis can generate approximately about 9 mg/min of crude ibuprofen. Addition of parallel reactors or lengthening the channels would permit a high throughput synthesis of ibuprofen. Potential scale-up of this method would also benefit from the precise temperature control (from 150° C. to 50° C. in sequential steps) and the excellent control of exotherms (caused by transitioning from pH 1 to 14). Performing this series of reactions on large scale in batch would be unfavorable due to the energy requirements needed to safely control these temperature changes and exotherms. It is conceivable that this methodology may be applied to other 2-arylpropionic acid derivatives, such as naproxen, and/or to develop recyclable, supported catalysts for the Friedel-Crafts acylation and 1,2-aryl migration.

According to another broad aspect of the present invention, an apparatus comprising two or three microreactors for the synthesis of ibuprofen is provided. According to some embodiments, an apparatus comprising two microreactors is provided for the synthesis of a precursor in the synthesis of ibuprofen, methyl-2-(4-isobutylphenyl)propanoate, which may be used with the following reageants: isobutylbenzene (IBB) and a "propionyl compound" as well as a strong acid, such as triflic acid. According to these embodiments, an apparatus is provided comprising a first microreactor and a second microreactor and a first junction and a second junction, wherein the first junction comprises a first inlet or input and a second inlet or input, wherein the first junction is attached to or continuous with the upstream side of the first microreactor, wherein the second junction comprises a third inlet or input attached to or continuous with the outlet of the first microreactor and a fourth inlet or input, wherein the second junction is attached to or continuous with the upstream side of the second microreactor, and wherein the second microreactor is positioned downstream of the first microreactor. According to some of these embodiments, the first and second inlets or inputs of the first junction and/or the fourth inlet or input of the second junction may each be open to the external environment of the apparatus for injecting or inputting one or more reagent stream(s). The first and second junctions may each be either a Y-junction or a T-junction. For example, the second junction may be T-junction which may also be packed with a solid material, such as glass beads. According to some embodiments, the temperatures of each of the microreactors may be controlled. For example, the temperature of the first microreactor may alternatively be about 50° C. or higher, about 100° C. or higher, or about 150° C. or higher, and/or the temperature of the second microreactor may be about 50° C. or higher. In addition, the temperature of a junction may be controlled. For example, the temperature of the second junction may be about 0° C.

According to some embodiments, an apparatus for the synthesis of ibuprofen is provided comprising the apparatus described above and further comprising a third microreactor and a third junction, wherein the third junction comprises a fifth inlet or input and a sixth inlet or input, wherein the fifth inlet or input is attached to or continuous with outlet of the second microreactor, and wherein the third microreactor is positioned downstream of the second microreactor. According to some of these embodiments, the sixth inlet or input of the third junction may be open to the external environment of the apparatus for injecting or inputting a reagent stream. The third junction may be either a Y-junction or a T-junction. For example, the third junction may be T-junction. According to some embodiments, the temperatures of the third microreactor may be controlled. For example, the temperature of the third microreactor may be about 65° C. or higher.

According to some embodiments, an apparatus comprising two microreactors is provided for the synthesis of ibuprofen, which may be used with the following reageants: 4-isobutyl-propiophenone (compound 2) as well as an "iodine-containing molecule" and TMOF in MeOH. According to these embodiments, an apparatus is provided comprising a first microreactor and a second microreactor and a first junction and a second junction, wherein the first junction comprises a first inlet and a second inlet, wherein the first junction is attached to or continuous with the upstream side of the first microreactor, wherein the second junction comprises a third inlet attached to or continuous with the outlet of the first microreactor and a fourth inlet, wherein the second junction is attached to or continuous with the upstream side of the second microreactor, and wherein the second microreactor is positioned downstream of the first microreactor. According to some of these embodiments, the first and second inlets of the first junction and/or the fourth inlet of the second junction may each be open to the external environment of the apparatus for injecting or inputting one or more reagent stream(s). The first and second junctions may each be either a Y-junction or a T-junction. For example, the first and/or second junction(s) may be T-junction. According to some embodiments, the temperatures of each of the microreactors may be controlled. For example, the temperature of the first microreactor may be about 50° C. or higher, and/or the temperature of the second microreactor may be about 65° C. or higher. In addition, the temperature of a junction may be controlled. For example, the temperature of the first junction may be about 0° C.

According to embodiments of the present invention, the tubing, unions, and junctions of a microreactor apparatus may each or all comprise, or be made of, a resistant polymeric material, such as a polymer made of a resistant thermoplastic resin, such as a DuPont® fluoropolymer including Teflon® PFA, etc, or a metal material. The diameters of the channels of the microreactors and/or junctions may each be in a range of between about 100 microns and about 1 centimeter.

According to embodiments of the present invention, the various flow rates of reaction components or reagent streams may be varied or controlled by application of a manual or automated syringe, pump, etc. Thus, according to some embodiments, a syringe, pump, or additional tubing may be attached to the one or more external inputs or inlets of the junctions. According to some embodiments, one or more of the following may be open to an external environment of the apparatus and/or may be attached to one or more syringes and/or pumps: the first inlet of the first junction, the second inlet of the first junction, the fourth inlet of the second junction, and/or the sixth inlet of the third junction. According to embodiments of the present invention, the apparatus may be manually controlled and/or automated by a machine. When the apparatus is automated, such operation may be under the control of a computer, which may be instructed by computer software. The flow rates of reaction components or reagent streams may be dynamically controlled, especially at the external inputs or inlets of the junctions.

EXAMPLES

The following is a description of an embodiment of the present invention for the continuous flow synthesis of ibuprofen. See FIG. 6. In one syringe is placed a solution of IBB (e.g., about 4.3 M) and propionic acid (e.g., about 4.3 M), and in another syringe is placed neat TfOH (e.g., about 11.3 M). The IBB/propionic acid syringe is set to 15.1 µL min$^{-1}$ (64.9 µmol min$^{-1}$) and the TfOH syringe is set to 28.7 µL min$^{-1}$ (324.6 µmol min$^{-1}$). The reaction stream is allowed to pass through a 50 cm segment of PFA tubing submerged into an oil bath set to about 150° C. To the outlet of the first reactor is attached an ETFE tee. A solution of PhI(OAc)$_2$ (e.g., about 0.5 M) and TMOF (e.g., about 2.0 M) in MeOH is placed in a syringe and set to 131.5 µL min$^{-1}$ (e.g., about 65.8 µmol PhI(OAc)$_2$ min$^{-1}$ and about 259.6 µmol TMOF min$^{-1}$) and connected to the tee. The tee is submerged in an ice bath, and the outlet of the tee is connected to an 80 cm segment of PFA tubing and submerged into an oil bath set to about 50° C. To the outlet of the second reactor is attached an ETFE tee using a flangeless nut. A solution of KOH (e.g., about 5.0 M) in MeOH/H$_2$O (about 4:1 v/v) is placed in a syringe and set to about 260.0 µL min$^{-1}$ (about 1300.0 µmol min$^{-1}$). The outlet of the tee was connected to a 300 cm segment of PFA tubing submerged into a water bath set to about 65° C.

The reaction is collected in a 100 mL round bottom flask. Once the collection is complete, DI H$_2$O (e.g., about 25 mL) is added to the round bottom flask, and the methanol is evaporated using rotary evaporation. The aqueous phase is washed with Et$_2$O (e.g., 3× about 30 mL), acidified with concentrated HCl and extracted with Et$_2$O (e.g., 3× about 30 mL). The organic extracts were repeatedly washed with DI H$_2$O (e.g., 5× about 20 mL) until the pH of the aqueous phase is neutral. The organic extracts are subsequently washed with brine (e.g., 1× about 20 mL), dried over Na$_2$SO$_4$, filtered, concentrated and dried to yield a light orange solid (about 68% crude yield, average of three trials; about 96% purity by GC and GC/MS). A seed crystal is added to initiate crystallization. The solid is dissolved in Et$_2$O and treated with activated carbon. The activated carbon is removed by filtering the suspension through a plug of anhydrous MgSO$_4$. The Et$_2$O is concentrated to yield an off-white solid, which is recrystallized with warm heptane. The filtrate is removed, and the crystals are dried under vacuum to afford ibuprofen as an off-white solid (51% yield, average of three trials, 99% purity by GC and GC/MS). Additional charcoal treatments may be performed to remove residual color after recrystallization without impacting yield: $^1$H NMR (300 MHz, CDCl$_3$): δ 7.23 (d, 2H), 7.13 (d, 2H), 3.71 (m, 4H), 2.48 (d, 2H), 1.86 (m, 1H), 1.52 (d, 3H), 0.93 (d, 6H); $^{13}$C NMR (75 MHz, CDCl$_3$): δ 175.4, 140.7, 137.9, 129.5, 127.3, 52.1, 45.21, 45.18, 30.3, 22.6, 18.8. MS m/z 220 (M+).

Having described embodiments of the present invention, it will be apparent that modifications and variations are possible without departing from the scope of the invention defined in the appended claims. Furthermore, it should be appreciated that all examples in the present disclosure, while illustrating embodiments of the present invention, are provided as non-limiting examples and are, therefore, not to be taken as limiting the various aspects so illustrated. Accordingly, it is intended that the present invention not be limited to the described embodiments but that it has the full scope defined by the language of the following claims and equivalents thereof.

What is claimed is:

1. A method comprising the following steps:
   (a) reacting isobutylbenzene with a propionyl compound in the presence of a strong acid to produce a first product; and
   (b) reacting the first product with trimethyl orthoformate (TMOF) and an iodine-containing molecule to form a second product,
   wherein steps (a) and (b) are performed sequentially without an intervening isolation or purification step, and wherein step (b) is performed after step (a), and wherein the strong acid is a Brønsted acid.

2. The method of claim 1, wherein step (a) comprises a Friedel-Crafts acylation reaction.

3. The method of claim 1, wherein the ratio of equivalents of the strong acid to isobutylbenzene reacted in step (a) is about 3:1 or greater.

4. The method of claim 1, wherein the ratio of equivalents of the strong acid to isobutylbenzene mixed in step (a) is about 5:1 or greater.

5. The method of claim 1, wherein the temperature of the reaction in step (a) is about 50° C. or higher.

6. The method of claim 5, wherein the temperature of the reaction in step (a) is about 100° C. or higher.

7. The method of claim 5, wherein the temperature of the reaction in step (a) is about 150° C. or higher.

8. The method of claim 1, wherein the propionyl compound comprises propionic acid, propionyl anhydride, or propionyl chloride.

9. The method of claim 1, wherein the strong acid has a pKa of less than or equal to about 1.0.

10. The method of claim 1, wherein the strong acid is triflic acid.

11. The method of claim 1, wherein the first product is 4-isobutylpropiophenone.

12. The method of claim 1, wherein step (b) comprises a 1,2-aryl migration reaction.

13. The method of claim 1, wherein the ratio of equivalents of the TMOF to the iodine-containing molecule reacted in step (b) is about 4:1 or greater.

14. The method of claim 1, wherein the temperature of the reaction in step (b) is about 50° C. or higher.

15. The method of claim 1, further comprising the step of (c) cooling the temperature of the reaction mixture comprising the first product of the reaction in step (a) and the TMOF and the iodine-containing molecule to about 0° C. just prior to step (b).

16. The method of claim 15, wherein step (c) is performed quickly or nearly instantaneously.

17. The method of claim 1, wherein the iodine-containing molecule comprises I$_2$ or PhI(OAc)$_2$.

18. The method of claim 1, wherein the second product is methyl-2-(4-isobutylphenyl)propanoate.

19. The method of claim 1, wherein steps (a) and (b) are performed in a microreaactor apparatus.

20. The method of claim 19, wherein the reaction in step (a) is performed in a first reagent stream in a first microreactor and the reaction in step (b) is performed in a second reagent stream in a second microreactor, and wherein the first microreactor is positioned upstream of the second microreactor.

21. The method of claim 20, wherein the isobutylbenzene and the propionyl compound are inputted into a first inlet of a first junction and the strong acid is inputted into a second inlet of the first junction, such that the isobutylbenzene, the propionyl compound, and the strong acid are combined into the first reagent stream in the first microreactor as a result of the outlet of the first junction being attached to or continuous with the inlet of the first microreactor.

22. The method of claim 20, wherein the first product of step (a) is inputted into a third inlet of a second junction attached to or continuous with the outlet of the first microreactor, and wherein the iodine-containing molecule and the TMOF are inputted into a fourth inlet of the second junction, such that the first product of step (a), the iodine-containing molecule and the TMOF are combined into the second reagent stream in the second microreactor as a result of the outlet of the second junction being attached to or continuous with the inlet of the second microreactor.

23. The method of claim 22, wherein the temperature of the second junction is about 0° C.

24. The method of claim 20, wherein the first reagent stream of the reaction in step (a) has a residence time in the first microreactor of about 5 minutes or greater.

25. The method of claim 20, wherein the second reagent stream of the reaction in step (b) has a residence time in the second microreactor of about 2 minutes or greater.

26. The method of claim 1, further comprising the step of (d) reacting the second product of the reaction in step (b) with a strong base or nucleophilic catalyst to form ibuprofen, wherein steps (a), (b), and (d) are performed sequentially without an intervening isolation or purification step, and wherein step (d) is performed after steps (a) and (b).

27. The method of claim 26, wherein the reaction in step (d) is a hydrolysis reaction.

28. The method of claim 26, wherein the strong base is a metal hydroxide.

29. The method of claim 26, wherein the nucleophilic catalyst comprises pyridine, DMAP or cyanide.

30. The method of claim 26, wherein the reaction in step (d) contains an excess amount of the strong base or nucleophilic catalyst.

31. The method of claim 30, wherein the amount of the strong base or nucleophilic catalyst is an amount sufficient to raise the pH to about 14.0.

32. The method of claim 26, wherein the ratio of the number of equivalents of the strong base added to the reaction in step (d) to the number of equivalents of the isobutylbenzene added to the reaction in step (a) is about 20:1 or greater.

33. The method of claim 26, wherein the ratio of the number of equivalents of the strong base added to the reaction in step (d) to the number of equivalents of the strong acid added to the reaction in step (a) is about 4:1 or greater.

34. The method of claim 26, wherein the ratio of the number of equivalents of the strong base added to the reaction in step (d) to the number of equivalents of the TMOF added to the reaction in step (b) is about 5:1 or greater.

35. The method of claim 26, wherein the temperature of the reaction in step (d) is about 65° C. or higher.

36. The method of claim 26, wherein steps (a), (b) and (d) are performed in a microreaactor apparatus.

37. The method of claim 36, wherein the reaction in step (a) is performed in a first reagent stream in a first microreactor, the reaction in step (b) is performed in a second reagent stream in a second microreactor, wherein the reaction in step (d) is performed in a third reagent stream in a third microreactor, and wherein the second microreactor is positioned downstream of the first microreactor and upstream of the third microreactor.

38. The method of claim 36, wherein the second product is inputted into a fifth inlet of a third junction and the strong base is inputted into a sixth inlet of the third junction, such that the second product and the strong base are combined into the third reagent stream of the third microreactor as a result of the outlet of the third junction being attached to or continuous with the inlet of the third microreactor.

39. The method of claim 36, wherein the third reagent stream of the reaction in step (d) has a residence time in the third microreactor of about 3 minutes or greater.

* * * * *